(12) United States Patent
Lo

(10) Patent No.: US 8,288,452 B2
(45) Date of Patent: Oct. 16, 2012

(54) SYNTHETIC BONE GRAFT BIOMATERIAL

(76) Inventor: Wei J. Lo, Nottingham (GB)

( * ) Notice: Subject to any disclaimer, the term of this patent is extended or adjusted under 35 U.S.C. 154(b) by 1328 days.

(21) Appl. No.: 11/273,927

(22) Filed: Nov. 15, 2005

(65) Prior Publication Data

US 2006/0122706 A1 Jun. 8, 2006

(51) Int. Cl.
*A61F 2/28* (2006.01)
*A61K 6/08* (2006.01)
(52) U.S. Cl. ........ 523/114; 523/210; 264/44; 623/23.56
(58) Field of Classification Search .................. 523/114, 523/210; 264/44; 623/23.56
See application file for complete search history.

(56) References Cited

U.S. PATENT DOCUMENTS

| | | | |
|---|---|---|---|
| 5,705,118 A | 1/1998 | Hayes et al. | |
| 6,210,625 B1 * | 4/2001 | Matsushita et al. | 264/610 |
| 6,379,962 B1 | 4/2002 | Holy et al. | |
| 6,479,418 B2 | 11/2002 | Li et al. | |
| 6,511,510 B1 | 1/2003 | de Bruijn et al. | |
| 6,605,648 B1 * | 8/2003 | Johnson et al. | 521/64 |
| 6,875,442 B2 * | 4/2005 | Holy et al. | 424/423 |
| 2002/0035402 A1 | 3/2002 | de Bruijn et al. | |
| 2003/0003160 A1 | 1/2003 | Pugh et al. | |
| 2003/0171822 A1 * | 9/2003 | Lo | 623/23.56 |
| 2004/0265350 A1 * | 12/2004 | Sambrook et al. | 424/423 |
| 2005/0119742 A1 * | 6/2005 | Richter et al. | 623/6.64 |

FOREIGN PATENT DOCUMENTS

| | | |
|---|---|---|
| EP | 0 987 032 A1 | 3/2000 |
| EP | 1 277 450 A2 | 1/2003 |
| WO | WO 97/46178 | 12/1997 |
| WO | WO 99/38542 | 8/1999 |
| WO | WO 00/30998 A1 * | 6/2000 |
| WO | WO 02/11781 A1 | 2/2002 |
| WO | WO 03/026714 A1 | 4/2003 |

OTHER PUBLICATIONS

Fabbri M et al, Hydroxyapatite-based porous aggregates: physico-chemical, nature, structure, texture and architecture, Biomaterials, Elsevier Science Publishers BV., Barking, GB, vol. 16, No. 3, Feb. 1, 1995, pp. 225-228, XP004033068 ISSN: 0142-9612 the whole document.

Joschek S et al, Chemical and physicochemical characterization of porous hydroxyapatite ceramics made of natural bone, Biomaterials, Elsevier Science Publishers BV., Barking, GB, vol. 21, No. 16, Aug. 2000, pp. 1645-1658, XP004200584 ISSN: 0142-9612.

Kim H-W et al, Hydroxyapatite/poly(epsilon-caprolactone) composite coatings on hydroxyapatite porous bone scaffold for drug delivery, Biomaterials, Elsevier Science Publishers BV., Barking, GB, vol. 25, No. 7-8, Mar. 2004, pp. 1279-1287, XP004475072 ISSN: 0142-9612 the whole document.

* cited by examiner

*Primary Examiner* — Tae H Yoon
(74) *Attorney, Agent, or Firm* — Ice Miller LLP

(57) ABSTRACT

A biomaterial comprising a ceramic material, the ceramic material having a plurality of connecting micropores of an average diameter of between 1 μm and 10 μm, substantially evenly distributed through the biomaterial. The ceramic particles are preferably partially fused to one or more adjacent ceramic particles to form a lattice defining micropores. Each particle preferably has an average diameter of 1 μm and 10 μm and may comprise a plurality of elongated macropores having an average diameter of between 150 μm and 500 μm. Further, the material may additionally contain midi-pores which are substantially spherical and have an average diameter of 5 μm and 150 μm. In addition, the application relates to a process for preparing a biomaterial comprising: (i) preparing a mixture of finely-divided biocompatible ceramic particles with a coating agent; (ii) causing the coating agent to coat the ceramic particles to form coated particles; (iii) causing the coated particles to form a body; and (iv) heating the body to eliminate residues of the coating agent, to partially fuse the ceramic particles and produce a fused biomaterial, and to biomaterials obtainable from the process and to the uses of the biomaterials.

25 Claims, 5 Drawing Sheets

Macropore    Midipore

SYNTHETIC BONE GRAFT BIOMATERIAL

CROSS REFERENCE TO RELATED APPLICATIONS

This application is a nationalization of International Application PCT/GB2004/001946, published as WO 2004/101013 and having a priority date of May 15, 2003.

BACKGROUND

The invention relates to a synthetic biomaterial comprising a ceramic material. The biomaterial has a porous structure which makes it suitable for use as, for example, synthetic bone grafts. This allows it to be used in orthopedic surgery, including vertebrae repair, musculoskeletal reconstruction, fracture repair, hip and knee reconstruction, osseous augmentation procedures and oral/maxillofacial surgery.

Synthetic materials for bone grafts are usually made of calcium phosphate ceramics and have a porous structure similar to that of cancellous bone. Many are derived from animals or marine life, such as from bovine bone or coral. These are intended to offer an interconnected macroporous structure and provide intensive osteoconductivity to regenerate and heal the host bone tissue. However, many of these have problems because their precise composition and structure cannot be controlled.

Such synthetic bone grafts typically come with interconnected "macropores", typically of 100-500 μm diameter. These provide a framework for the host bone to regenerate whilst reducing healing time. The pores allow bone tissue to grow into the bone graft. According to in vitro and in vivo experiments, the host's own bone tissue uses the macroporous structure to grow into the bone replacement material, the material being slowly degraded and being replaced by new bone growth. Ideally, biomaterials used for bone grafts should be microporous with a pore diameter of 1-10 μm. Such micropores have been found to improve the ability of osteoblasts and other cells from the host to bind to the synthetic biomaterial and to allow access of the cells to dissolve the sintered connections between the individual ceramic particles.

Typical commercially available synthetic bone grafts usually have a random distribution of pore sizes and no observable preferred orientation of the interconnected porous structure. Furthermore, they have little or no microporous structure.

For example, U.S. Pat. No. 6,511,510 discloses an osteoinductive biomaterial that is made from calcium phosphate or a glass ceramic. The material is stated to comprise micropores and macropores, the macropores preferably being interconnected. The micropores are only present on the surface of the material. The osteoinductive biomaterial is obtained by sintering a ceramic material. The material is preferably ground with sandpaper to remove chemical surface impurities and the material is then treated with an aqueous solution of an acid. The acid etches the surface of the material, especially the annealed particles' grains boundaries, to produce the micropores. Macropores may be formed using pore-forming agents such as hydrogen peroxide, baking powder or bicarbonate. Negative replica-forming agents such as wax or fiber are also disclosed which will not generate gas in the same way as hydrogen peroxide or baking powder, but will be burned to leave the same shape or pore as the original wax or fiber.

U.S. Pat. No. 6,479,418 discloses a method of preparing a porous ceramic body by mixing a slurry of a ceramic material with a viscous organic phase to obtain a dough, drying the dough and removing the organic phase by thermal decomposition. Foaming agents, such as sodium bicarbonate and citric acid may be used to create "macropores". The surface of the ceramic body, including the surface of the pores, is stated to have a microporous surface. This is shown in the document as being irregular depressions in the surface of the material surrounded by irregular clumps of fused ceramic particles.

Ceramic materials used to mould natural objects are disclosed in U.S. Pat. No. 5,705,118. The ceramic uses gluten and/or a number of other materials as a binder. This is mixed together as a batch with water or other liquid, prior to spraying or applying onto an object to produce a mould. This is fired to produce a porous body.

SUMMARY

The Applicants developed an alternative method of producing artificial bone which allowed the controlled formation of macropores, including the diameter and orientation of the macropores. This was published as WO 02/11781. The method used in that application prepared a mixture of finely divided bio-compatible ceramic powder, an organic binder and a pore-forming agent in an inert liquid to form a body, causing at least some of the macropores to align along a common axis, prior to heating to fix the porous structure and further heating to eliminate residues of the organic binder and pore-forming agent, and to fuse it. This method was shown to produce a series of tube-like macroporous structures. However, the inventors have found that the method used in WO 01/11781 does not allow the size and distribution of micropores to be controlled. Using the method of WO 02/11781 results in the clumping of ceramic particles and an uneven distribution of any micropores is formed.

They have now been able to identify a method of producing a biomaterial having a plurality of connecting micropores which are substantially evenly distributed through the entire cross-section of the ceramic material. This improves the ability of a recipient's cells to bind to the biomaterial and integrate it with the recipient's own bone or other tissue.

Accordingly, a first aspect of the invention provides a biomaterial comprising a ceramic material, the ceramic material having a plurality of connecting micropores of an average diameter of between 1 μm and 10 μm substantially evenly distributed through the ceramic material.

That is, the micropores are not confined to the surface of the biomaterial but are found substantially throughout a cross-section through the ceramic material.

Preferably, the average diameter of the micropores is between 2-8 μm, most preferably 5-6 μm.

The micropores may be irregular in shape. Accordingly, the diameter of the micropores, and indeed the macropores and midi-pores referred to below, are determined by adding the widest diameter of the pore to the narrowest diameter of the pore and dividing by 2.

Preferably, the ceramic material is evenly distributed through the cross-section, that is substantially without clumps of ceramic material forming.

Preferably, the biomaterial comprises a plurality of ceramic particles, each particle being partially fused to one or more adjacent ceramic particles to form a lattice defining the micropores.

Preferably, the biomaterial contains particles having an average particle diameter of 1-10 μm, more preferably at least 2 μm or 4 μm and/or less than 10 μm or less than 6 μm, most preferably 5-6 μm. This particle size range has been found to allow the controlled formation of the micropores.

The biomaterial may additionally comprise a plurality of elongated macropores having an average diameter of between 150-500 μm, more preferably 200-400 μm. That is, they preferably have a substantially circular cross-section, and are tube-like. These macropores may have an average length of between 300-3000 μm, more preferably at least 300 μm, at least 400 μm or at least 500 μm and/or less than 3000 μm, less than 2000 μm, less than 1000 μm, or less than 800 μm, most preferably 500-1000 μm. At least a portion of the macropores are preferably interconnecting.

The biomaterial may additionally comprise a plurality of midi-pores within walls that are formed between the macropores. Midi-pores are substantially spherical pores which are typically approximately 5-150 μm, especially 50-100 μm or 60-100 μm in diameter. They substantially increase the total porosity without compromising the mechanical strength of the materials. Furthermore, the midi-pores can be beneficently used to deliver drugs, cell growth factors or other biologically active agents.

The macropores and midipores are preferably themselves interconnected via a plurality of micropores. That is, the macropores, and where present midipores, may be in fluid connection with each other via micropores, instead of or in addition to the interconnected macropores.

The average porosity of the biomaterial is preferably at least 50%, more preferably greater than 60%, most preferably between 70-75% average porosity.

Preferably, the biomaterial has a compressive strength of at least 1.0 MPa to preferably 10 MPa, more preferably 1.5 MPa, 2 MPa, 3 MPa, 4 MPa, 5 MPa, most preferably between 6 MPa and 7 MPa. Compressive strength may be detected using techniques known in the art. Typically 1 cm$^3$ of sample is compressed.

The inventors have been able to produce biomaterials having reduced wall thicknesses between each macropore. This improves the ability of the biomaterial to be incorporated into the host. Accordingly, preferably the average thickness of ceramic material between each macropore is 20-200 μm, most preferably 50-150 μm, more preferably 50-100 μm.

The biomaterial may additionally comprise one or more pharmaceutically or biologically active compounds. These may be incorporated into the pores and in use may be used to stimulate cell growth around and into the biomaterial. For example, growth factors, such as transforming growth factor (TGF-P1), bone morphogenetic protein (BMP-2) or osteogenic protein (OP-1) may be incorporated into the biomaterial. Further materials such as enzymes, vitamins (including Vitamin D) and trace material such as zinc (for example in the form of salt) may also be incorporated.

Preferably the product is bread-like in cross-section with macropores and micropores.

The ceramic material used may be any non-toxic ceramic known in the art, such as calcium phosphate and glass ceramics. Preferably the ceramic is not a silicate. Most preferably the ceramic material is a calcium phosphate, especially a- or J3-tricalcium phosphate or hydroxyapatite, or mixtures thereof. Most preferably, the mixture is hydroxyapatite and (3-tricalcium phosphate, especially more than 50% w/w hydroxyapatite, most preferably 70% hydroxyapatite and 30% 13-tricalcium phosphate.

A second aspect of the invention provides a process for preparing a biomaterial, such as the biomaterial according to the first aspect of the invention, which comprises:
1. preparing a mixture of finely divided bio compatible ceramic particles with a coating agent;
2. causing the coating agent to coat the ceramic particles to form coated particles; (iii) causing the coated particles to form a body; and
3. heating the body to eliminate residues of the coating agent and to partially fuse the ceramic particles, thereby to produce a fused biomaterial.

The inventors have found that coating the particles improves the distribution of the particles through the finely fused product and produces a substantially oviform product with substantially evenly distributed micropores.

Suitable coating agents include those comprising starch, agar, polyethylene glycol (PEG), hydroquinone, ethyl cellulose or tetrapropylanunonium. The starch is preferably provided as corn flour, potato starch or rice powder, most preferably tapioca powder.

Where the coating agent is liquid, for example PEG, simply mixing the ceramic particles in the coating agent may coat the particles. Alternatively, some coating agents, such as the starch and agar coating agents may be mixed with an inert liquid, such as water, in a powder form, and heated to allow the starch or agar to form a polymer coating around the particles. Heating liquids containing starch causes the starch to polymerise and causes it to thicken the liquid in a similar manner to adding corn flour to thicken gravy when cooking.

The inventors have found that where the mixture of ceramic particles and coating agent needs to be heated, then it is convenient to mix the components, including where necessary the inert liquid, and then heat the mixture in a steam generator, such as a rice cooker. Heating the mixture in steam allows the mixture to be heated in a controlled manner, whilst allowing the mixture to remain moist. The time will, of course, vary depending on the quantities used. Heating such mixtures of material, typically produces a body having a dough-like consistency. Preferably the mixture is heated to about 100° C. for typically 20-30 minutes.

The body is finally heated to eliminate residues of the coating agent and to partially fuse the ceramic particles to produce a fused biomaterial. This final heating step is also known as an annealing or sintering step and typically uses temperatures of about 1200° C. to about 1450° C., preferably 1200-1350° C. Temperature and duration of heating will depend upon the size of the sample and the initial ceramic concentration and the type of ceramic material used. Furthermore, the temperature is controlled to prevent fusion of the micropores. Typically, the body is annealed for 1 to 2 hours.

Typically the weight ratio between the ceramic powder and the total amount of carbohydrate and gluten powder is between about 1.087 to about 1.163. The weight ratio of ceramic powder to inert liquid is typically about 1.042 to 1.316.

This process, as well as producing the biomaterial of the first aspect of the invention, has been found to reduce the appearance of large voids within the material, thus reducing wastage of biomaterial which would otherwise be disposed of due to the voids.

The ceramic particles may also be mixed, prior to coating, with a dispersing agent. The dispersing agent allows the ceramic powder to be homogeneously mixed with, for example, the inert liquid such as water. Without the dispersing agent, the ceramic particles will separate from the water within minutes. The function of the dispersing agent is to prevent the precipitation of the powder and to allow it to be homogeneously dispersed within the water.

Preferred dispersing agents include acid-based solutions, polymers such as phosphates and acrylate polymers, ammonia, phosphoric acids such as orthophosphoric acid, or an ammonium salt of an acrylate or methacrylate polymer such as ammonium polyacrylate and ammonium polymethacrylate. Relatively small amounts of the dispersing agent need be used, for example for 100 ml. of inert liquid only 0.5 ml. to 1 ml. of dispersing agent may be required.

The body formed from the coated particles may be mixed with an organic binder prior to the final heating step. The organic binder is preferably a carbohydrate powder, such as corn flour or wheat flour. However, the inventor has identified that adding high-gluten flours (also known as strong flours), or indeed extracted gluten, improves formation of the final product. Gluten is the reserve protein of seeds, such as wheat grain. Typically, it contains at least 85% protein and is a mixture of gliadin and glutenin, along with globulin and albumin.

If it is desired to form macropores, then it is necessary to use a pore-forming agent. This agent is allowed to form a pore-forming structure in the body and then is heated to fix the porous structure. This heating step may be at a lower temperature than the final sintering step, typically 100, 130 or 150-230° C. This is preferably in a humidity-controlled oven, for example in steam. Generally, this stabilization of the pore-forming structure can be achieved in less than 1 hour, generally 5-50 minutes, for example 15-45 minutes. This will vary depending on the size of the body.

The pore-forming agent may be mixed with the organic binder and the body may be a chemical pore-forming agent such as hydrogen peroxide, disodium diphosphate or sodium bicarbonate. However, most preferably the pore-forming agent is a micro-organism such as a yeast or bacterium. Such micro-organisms preferably form carbon dioxide by metabolizing a carbohydrate, such as a sugar which may be added to the organic binder. The advantage of using a micro-organism is that the size of the macropores may be carefully controlled. Furthermore, the pore-forming action of the micro-organism can be easily stopped simply by heating the body to kill the micro-organism.

If yeast is used, then preferably a yeast enhancer is also incorporated into the organic binder.

Preferably, there is a step of additionally causing at least some of the pore-forming agent to align along a common axis. This may be achieved, for example, by placing the body containing the pore-forming agent into an elongated mould with space to expand at the ends of the mould. The pore-forming agent, such as yeast, is allowed to produce the pores within the confines of the sides of mould, thus forcing the body to elongate along the length of the mould. Alternatively, the pore-forming agent may be aligned simply be extruding the body. This is also described in WO 02/11781.

The ceramic particles are preferably as defined for the first aspect of the invention.

The process preferably comprises a step of additionally incorporating a biologically or pharmaceutically active compound into or onto the fused biomaterial. These compounds are preferably as defined for the first aspect of the invention. They may simply be incorporated by soaking the fused body into a suitable solution containing the biologically or pharmaceutically active compound, prior to drying the product. This allows, for example, the active compound to diffuse within the micropores, midi-pores and macropores of the product.

The invention also includes within its scope biological material obtainable by the process of the invention. Bone implants, dental implants, ear, nose and throat implants comprising the biomaterial, or indeed other implants, are also included within the scope of the invention. The use of the biomaterial as a bone replacement, tooth implant or maxillofacial repair material is also included within the invention.

Methods of inducing bone formation in a mammal by implanting a biomaterial according to the invention into a mammal in a manner to induce bone formation on and/or within the biomaterial, are also provided by the invention.

The biomaterial of the invention has been found to have improved bio-compatibility and promotes bone in-growth and cell attachment.

BRIEF DESCRIPTION OF THE DRAWINGS

The invention will now be described by way of example only, with reference to the following figures.

The figures show that the coating step of the invention produces thinner connecting walls, better defined macropores and substantially evenly distributed micropores.

Figure 1B:
FIGS. 1A to 1C show samples of biomaterial prepared without the step of coating the ceramic particles prior to fusing.
Figure 1A:
Figure 1D:
FIG. 1D shows a sample prepared using the additional coating step of the invention.
Figure 1C:
Figure 2A:
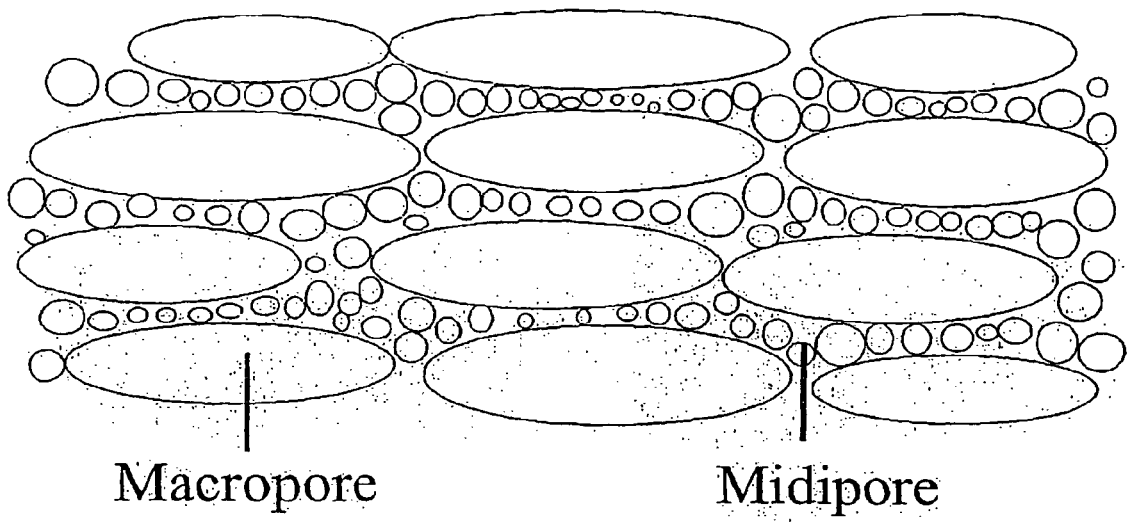

FIG. 2A is a schematic diagram which shows the theoretical porous structure of Orthogem's synthetic bone graft. The midipores make up the porous connected walls between the macropores.

Figure 2B:
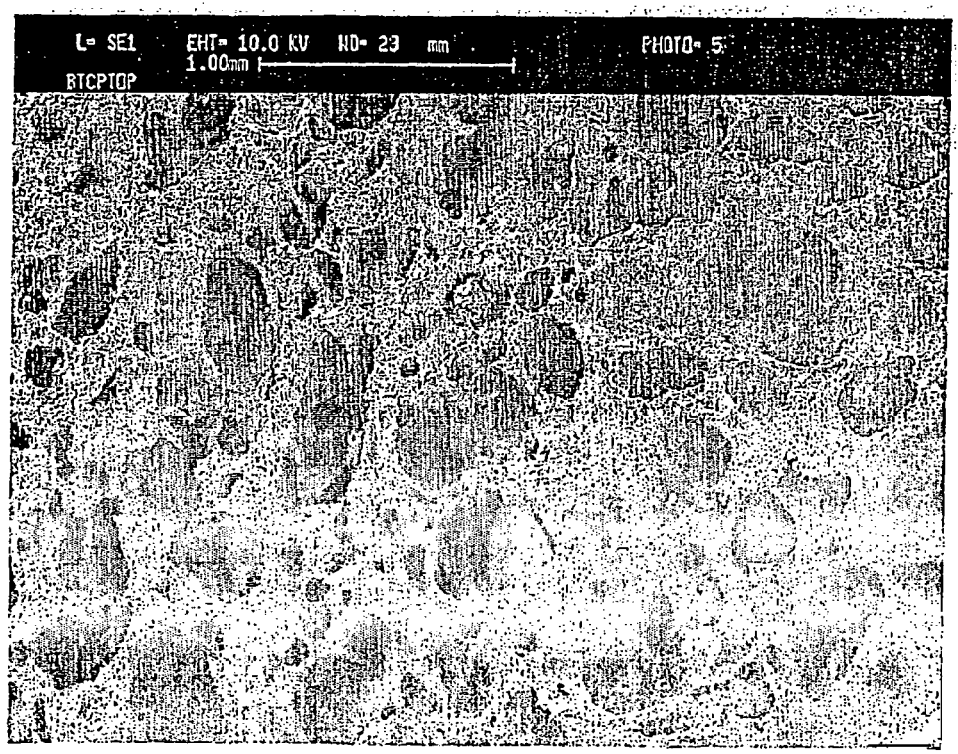

FIG. 2B is scanning electron microscope (SEM) picture at magnification 60× which shows the 2-D cross section of the actual materials. The midipores can be easily identified.

Figure 2C:
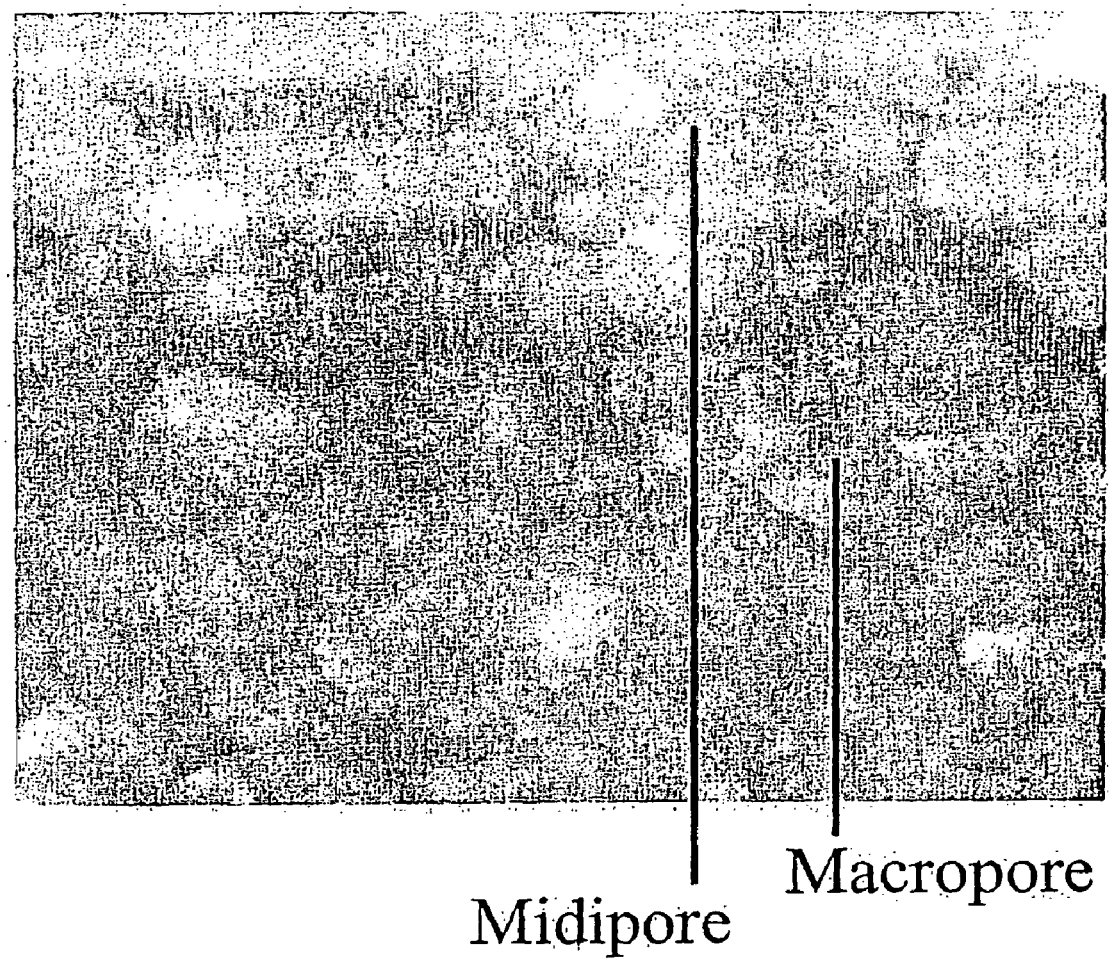

FIG. 2C is a back light optical microscope picture at magnification 60× shows the 3-D porous structure of the materials. The picture shows the macropores are interconnected and midipores appeared among the macropores.

Figure 2D:
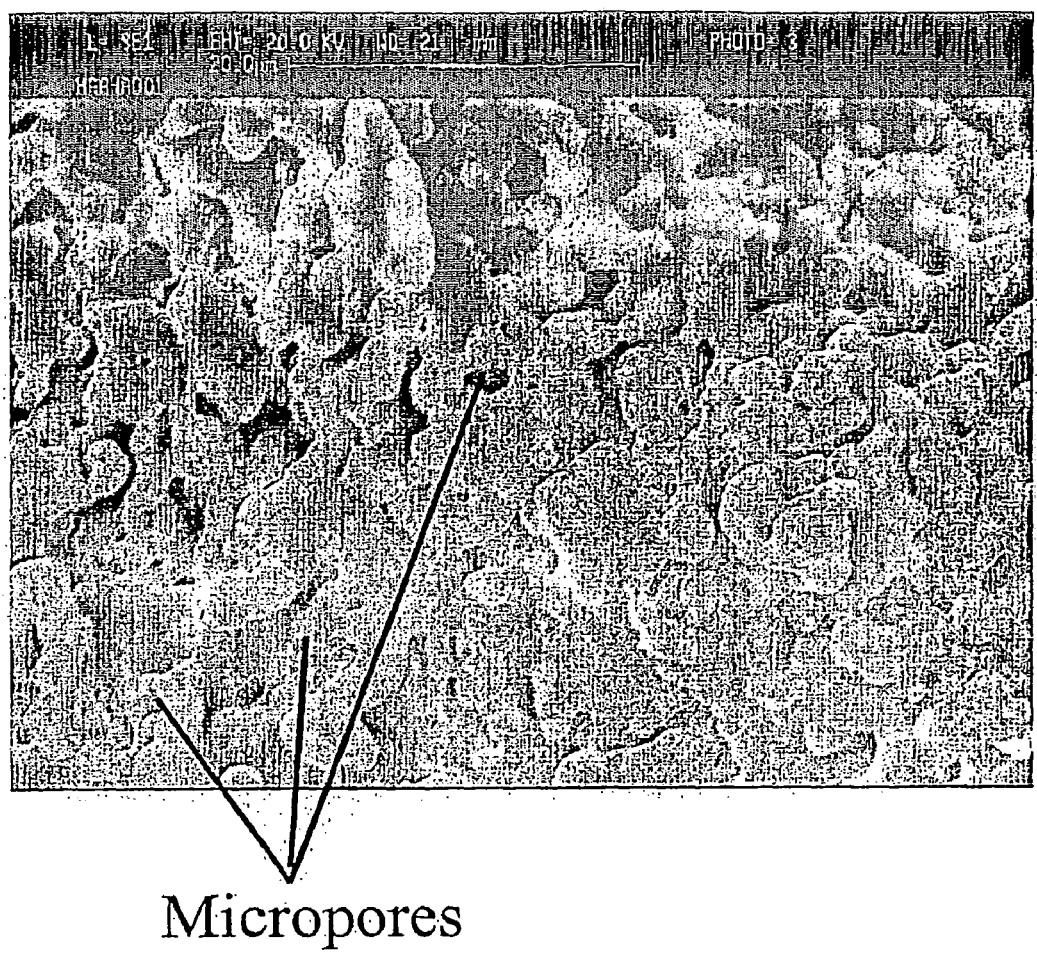

FIG. 2D is a SEM imagine at magnification 2000× which shows the microporous structures which are substantially throughout the whole materials.

DESCRIPTION

According to one aspect of the present invention, and exemplary embodiment of the present invention is disclosed below:

EXAMPLE

Hydroxyapatite powder is mixed with water (38 ml.), and a dispersing agent (1 ml.).

Tapioca (9 g.) or other coating agent is then blended into the mixture within a heatproof vessel. This produces a liquid suspension or slurry. The mixture is then placed within a. steamer, such as a rice cooker, and heated to approximately 100° C. A steamer, such as a rice cooker, is particularly advantageous because it prevents the material drying out. This produces a moist "dough".

A mixture of wheat gluten (13 g.) and white strong flour with a high gluten content (15 g.) optionally, together with a yeast enhancer (vital wheat gluten, diastatic malt and ascorbic acid) and yeast (7 g.), such as *Saccharomyces cerevisiae, Schizosaccharoinyces pombe, Saccharomyces carisbergiensis* or another carbon dioxide producing micro-organism, is prepared. An additional source of carbohydrate, such as a sugar, may also be incorporated. This is mixed with the cooled dough of coated ceramic particles, together with a little water. The mixing may be carried out by hand or may also be mixed using, for example, a food processor. The mixture may then be compressed in order to exclude any large voids which have appeared within the mixture by mixing.

The final mixture again has a dough-like consistency. This may be placed within, for example, an elongated mould made of any suitable material, such as aluminum. By placing the dough within the mould with a space at each end of the elongated mould, the yeast produces carbon dioxide and causes the dough to expand along the length of the mould. The dough is prevented from expanding width-ways in the mould by the walls of the mould. Depending on the micro-organism used, the generation of carbon dioxide is achieved by "proving" in a similar manner to bread. That is, the dough is maintained at a temperature of 40-45° C. to allow the yeast to produce carbon dioxide. If another pore-forming agent, such as sodium bicarbonate is used, it may be advantageous to add an acid, such as citric acid, which reacts with the sodium bicarbonate to produce carbon dioxide.

The porous structure is set by heating, for example, to 100° C. in a steam cooker for approximately 20-25 minutes. This kills the yeast and also sets the organic binder, such as gluten. It also expands the dough to fit the mould, in a similar manner to bread dough which is expanded to fit a bread mould. Adjusting the size of the mould and ensuring that the mould is closed, rather than open-ended, allows the density of the product to be adjusted. The body with the fixed porous structure is then allowed to cool. At this stage it is possible to shape the material as it typically has a moist bread-like consistency and texture. It is therefore easily cut to a desired shape. Freezing or refrigerating the product at this stage improves the ability to shape the product. The shaped product is then sintered to a sufficiently high temperature to partially fuse the ceramic particles. This temperature will vary depending on the ceramic particles used. Typically, hydroxyapatite uses a temperature of 1350° C., tricalcium phosphate uses approximately 1200° C.

Using a mixture of hydroxyapatite and tricalcium phosphate has been found by the inventors to improve the rate at which cells distribute themselves through the product.

What is claimed is:

1. A biomaterial comprising a ceramic material, the ceramic material having a plurality of connecting micropores of an average diameter of between 1 μm and 10 μm substantially evenly distributed through the ceramic material, a plurality of elongated macropores having an average diameter of between 150 μm and 500 μm and an average length of between 300-3000 μm, and a plurality of substantially spherical midi-pores having an average diameter of 5 μm to 150 μm.

2. A biomaterial according to claim 1, composed of a plurality of ceramic particles, each particle being partially fused to one or more adjacent ceramic particles to form a lattice defining said micropores.

3. A biomaterial according to claim 2, wherein each particle has an average diameter of 1 μm to 10 μm.

4. A biomaterial according to claim 1 having an average porosity of at least 50%.

5. A biomaterial according to claim 1 having a compressive strength of at least 1.0 MPa.

6. A biomaterial according to claim 1, wherein the average thickness of ceramic material between each macropore is 20 to 200 μm.

7. A biomaterial according to claim 1 additionally comprising one or more biologically or pharmaceutically active compounds.

8. A biomaterial according to claim 7, wherein the pharmaceutically active compound is a cell growth factor or a bone morphogenetic protein, 9. A biomaterial according to claim 1, wherein the ceramic material comprises calcium phosphate.

10. A biomaterial according to claim 9, wherein the calcium phosphate is α or β tricalcium phosphate or hydroxyapatite or a mixture thereof.

11. A process for preparing a biomaterial which comprises:
(i) preparing a mixture of finely-divided biocompatible ceramic particles with a coating agent, wherein the coating agent comprises starch, agar, polyethylene glycol, hydroquinone, ethyl cellulose or tetrapropylammonium;
(ii) causing the coating agent to coat the ceramic particles to form coated particles;
(iii) causing the coated particles to form a body;
(iv) mixing the body with an organic binder, the organic binder comprising gluten; and
(v) heating the body to eliminate residues of the coating agent, to partially fuse the ceramic particles and produce a fused biomaterial.

12. A process according to claim 11, wherein the starch is provided as tapioca powder, cornflour, potato starch or rice powder.

13. A process for preparing a biomaterial which comprises:
(i) preparing a mixture of finely-divided biocompatible ceramic particles with a coating agent,;
(ii) heating the mixture to cause the coating agent to coat the ceramic particles to form coated particles;
(iii) causing the coated particles to form a body;
(iv) mixing the body with an organic binder, the organic binder comprising gluten; and
(v) heating the body to eliminate residues of the coating agent, to partially fuse the ceramic particles and produce a fused biomaterial.

14. A process according to claim 11, comprising mixing a dispersing agent with the finely divided biocompatible ceramic particles.

15. A process according to claim 11, additionally comprising the steps of mixing the body with a pore-forming agent, allowing the pore-forming agent to form a pore-forming structure, and heating the body to fix the porous structure, prior to heating to partially fuse the ceramic particles.

16. A process according to claim 15, wherein the pore-forming agent is a micro-organism.

17. A process according to claim 16, additionally comprising the step of causing at least some of the pore-forming agent to align along a common axis.

18. A process according to claim 11, wherein the ceramic particles have an average diameter of 1 μm to 10 μm.

19. A process according to claim 11, wherein the ceramic particles are calcium phosphate.

20. A process according to claim 19, wherein the calcium phosphate is α or β tricalcium phosphate or hydroxyapatite or a mixture thereof.

21. A process according to claim 11, comprising the step of shaping the body prior to fusing it, 22. A process according to claim 11 additionally comprising the step of incorporating a biologically or pharmaceutically active compound into or onto the fused biomaterial.

23. A process according to claim 22, wherein the pharmaceutically active compound is a cell growth factor or a bone morphogenetic protein.

24. A bone implant, dental implant or an ear, nose or throat (ENT) implant comprising a biomaterial according to claim 1.

25. A method of using a biomaterial according to claim 1 as a bone replacement in a dental implant or maxillo facial repair material.

* * * * *